US007670623B2

(12) United States Patent
Kotha et al.

(10) Patent No.: US 7,670,623 B2
(45) Date of Patent: Mar. 2, 2010

(54) HEMOSTATIC COMPOSITION

(75) Inventors: Sanjay Kotha, Falls Church, VA (US); Tirumalai S. Sudarshan, Vienna, VA (US)

(73) Assignee: Materials Modification, Inc., Fairfax, VA (US)

(*) Notice: Subject to any disclaimer, the term of this patent is extended or adjusted under 35 U.S.C. 154(b) by 357 days.

(21) Appl. No.: 10/157,921

(22) Filed: May 31, 2002

(65) Prior Publication Data

US 2003/0224056 A1   Dec. 4, 2003

(51) Int. Cl.
*A61K 38/00* (2006.01)
*A61K 9/14* (2006.01)

(52) U.S. Cl. .......................................... 424/489; 514/2

(58) Field of Classification Search ................. 424/400, 424/489, 490; 600/9, 12
See application file for complete search history.

(56) References Cited

U.S. PATENT DOCUMENTS

| | | | |
|---|---|---|---|
| 3,047,507 A | 7/1962 | Winslow | |
| 3,127,528 A | 3/1964 | Lary et al. | |
| 3,287,677 A | 11/1966 | Mohr | |
| 3,488,531 A | 1/1970 | Rosensweig | |
| 3,560,378 A | 2/1971 | Weiss et al. | |
| 3,767,783 A | 10/1973 | Sweeny et al. | |
| 3,927,329 A | 12/1975 | Fawcett et al. | |
| 3,937,839 A | 2/1976 | Strike et al. | |
| 4,064,409 A | 12/1977 | Redman | |
| 4,106,488 A | 8/1978 | Gordon | |
| 4,107,288 A | 8/1978 | Oppenheim et al. | |
| 4,183,156 A | 1/1980 | Rudy | |
| 4,219,945 A | 9/1980 | Rudy | |
| 4,267,234 A | 5/1981 | Rembaum | |
| 4,268,413 A | 5/1981 | Dabisch | |
| 4,303,636 A | 12/1981 | Gordon | |
| 4,321,020 A | 3/1982 | Mittal | |
| 4,323,056 A | 4/1982 | Borrelli et al. | |
| 4,340,626 A | 7/1982 | Rudy | |
| 4,342,157 A | 8/1982 | Gilbert | |
| 4,364,377 A * | 12/1982 | Smith .......................... 600/12 | |
| 4,443,430 A | 4/1984 | Mattei et al. | |
| 4,452,773 A | 6/1984 | Molday | |
| 4,454,234 A | 6/1984 | Czerlinski | |
| 4,472,890 A | 9/1984 | Gilbert | |
| 4,501,726 A | 2/1985 | Schröder et al. | |
| 4,545,368 A | 10/1985 | Rand et al. | |
| 4,554,088 A | 11/1985 | Whitehead et al. | |
| 4,574,782 A | 3/1986 | Borrelli et al. | |
| 4,613,304 A | 9/1986 | Meyer | |
| 4,628,037 A | 12/1986 | Chagnon et al. | |
| 4,637,394 A | 1/1987 | Racz et al. | |
| 4,662,359 A | 5/1987 | Gordon | |
| 4,672,040 A | 6/1987 | Josephson | |
| 4,695,392 A | 9/1987 | Whitehead et al. | |
| 4,695,393 A | 9/1987 | Whitehead et al. | |
| 4,721,618 A | 1/1988 | Giles et al. | |
| 4,770,183 A * | 9/1988 | Groman et al. ............ 424/9.32 | |
| 4,834,898 A | 5/1989 | Hwang | |
| 4,951,675 A | 8/1990 | Groman et al. | |
| 4,992,190 A | 2/1991 | Shtarkman | |
| 4,999,188 A | 3/1991 | Solodovnik et al. | |
| 5,067,952 A | 11/1991 | Gudov et al. | |
| 5,069,216 A | 12/1991 | Groman et al. | |
| 5,079,786 A | 1/1992 | Rojas | |
| 5,108,359 A | 4/1992 | Granov et al. | |
| 5,161,776 A | 11/1992 | Nicholson | |
| 5,178,947 A * | 1/1993 | Charmot et al. ............ 428/405 | |
| 5,180,583 A | 1/1993 | Hedner | |
| 5,202,352 A | 4/1993 | Okada et al. | |
| 5,207,675 A | 5/1993 | Canady | |
| 5,236,410 A | 8/1993 | Granov et al. | |
| 5,348,050 A | 9/1994 | Ashton | |
| 5,354,488 A | 10/1994 | Shtarkman | |
| 5,358,659 A | 10/1994 | Ziolo | |
| 5,374,246 A | 12/1994 | Ray | |
| 5,427,767 A | 6/1995 | Kresse et al. | |
| 5,466,609 A | 11/1995 | Siiman et al. | |
| 5,493,792 A | 2/1996 | Bates et al. | |
| 5,507,744 A | 4/1996 | Tay et al. | |
| 5,525,249 A | 6/1996 | Kordonsky et al. | |
| 5,549,837 A | 8/1996 | Ginder et al. | |
| 5,565,215 A | 10/1996 | Gref et al. | |
| 5,582,425 A | 12/1996 | Skanberg et al. | |
| 5,595,735 A | 1/1997 | Saferstein et al. | |
| 5,597,531 A | 1/1997 | Liberti et al. | |
| 5,599,474 A | 2/1997 | Weiss et al. | |
| 5,624,685 A | 4/1997 | Takahashi et al. | |
| 5,635,162 A | 6/1997 | Fischer | |
| 5,635,215 A | 6/1997 | Boschetti et al. | |
| 5,645,849 A | 7/1997 | Pruss et al. | |
| 5,646,185 A | 7/1997 | Giaccia et al. | |
| 5,650,681 A | 7/1997 | DeLerno | |
| 5,667,715 A | 9/1997 | Foister | |
| 5,670,078 A | 9/1997 | Ziolo | |
| 5,673,721 A | 10/1997 | Alcocer | |

(Continued)

FOREIGN PATENT DOCUMENTS

CA        2328826 A1    3/2001

(Continued)

OTHER PUBLICATIONS

Remington: The Science and Practice of Pharmacy, vol. II, 1524-1528 (1995).*

(Continued)

*Primary Examiner*—Jake M Vu
(74) *Attorney, Agent, or Firm*—Dinesh Agarwal, P.C.

(57) ABSTRACT

A hemostatic composition includes a carrier medium including a predetermined amount of a particulate material. The particulate material is comprised of core particles with a coating. The core particles have an average particle size of about 5 nm to 10 μm, and the coating is one of gold, silica, silver, platinum, steel, cobalt, carbon, a polymer, or a combination thereof.

31 Claims, 2 Drawing Sheets

U.S. PATENT DOCUMENTS

| | | | |
|---|---|---|---|
| 5,695,480 A | 12/1997 | Evans et al. | |
| 5,702,630 A | 12/1997 | Sasaki et al. | |
| 5,707,078 A | 1/1998 | Swanberg et al. | |
| 5,707,877 A | 1/1998 | Siiman et al. | |
| 5,714,829 A | 2/1998 | Guruprasad | |
| 5,782,954 A | 7/1998 | Luk | |
| 5,800,372 A | 9/1998 | Bell et al. | |
| 5,813,142 A | 9/1998 | Demon | |
| 5,900,184 A | 5/1999 | Weiss et al. | |
| 5,919,490 A | 7/1999 | Zastrow et al. | |
| 5,927,753 A | 7/1999 | Faigle et al. | |
| 5,947,514 A | 9/1999 | Keller et al. | |
| 5,958,794 A | 9/1999 | Bruxvoort et al. | |
| 5,993,358 A | 11/1999 | Gureghian et al. | |
| 6,013,531 A | 1/2000 | Wang et al. | |
| 6,027,664 A | 2/2000 | Weiss et al. | |
| 6,036,226 A | 3/2000 | Brown et al. | |
| 6,036,955 A | 3/2000 | Thorpe et al. | |
| 6,039,347 A | 3/2000 | Maynard | |
| 6,044,866 A | 4/2000 | Rohrbeck | |
| 6,051,607 A | 4/2000 | Greff | |
| 6,076,852 A | 6/2000 | Faigle | |
| 6,083,680 A | 7/2000 | Ito et al. | |
| 6,096,021 A | 8/2000 | Helm et al. | |
| 6,136,428 A | 10/2000 | Truong et al. | |
| 6,149,576 A | 11/2000 | Gray et al. | |
| 6,149,832 A | 11/2000 | Foister | |
| 6,167,313 A | 12/2000 | Gray et al. | |
| 6,186,176 B1 | 2/2001 | Gelbmann | |
| 6,189,538 B1 | 2/2001 | Thorpe | |
| 6,207,178 B1 | 3/2001 | Westesen et al. | |
| 6,225,705 B1 | 5/2001 | Nakamats | |
| 6,266,897 B1 | 7/2001 | Seydel et al. | |
| 6,274,121 B1 | 8/2001 | Pilgrimm | |
| 6,299,619 B1 | 10/2001 | Greene, Jr. et al. | |
| 6,312,484 B1 | 11/2001 | Chou et al. | |
| 6,315,709 B1 | 11/2001 | Garibaldi et al. | |
| 6,319,599 B1 | 11/2001 | Buckley | |
| 6,335,384 B1 | 1/2002 | Evans et al. | |
| 6,355,275 B1 | 3/2002 | Klein | |
| 6,358,196 B1 | 3/2002 | Rayman | |
| 6,364,823 B1 | 4/2002 | Garibaldi et al. | |
| 6,391,343 B1 * | 5/2002 | Yen | 424/491 |
| 6,399,317 B1 | 6/2002 | Weimer | |
| 6,409,851 B1 | 6/2002 | Sethuram et al. | |
| 6,443,993 B1 | 9/2002 | Koniuk | |
| 6,468,730 B2 | 10/2002 | Fujiwara et al. | |
| 6,475,710 B2 | 11/2002 | Kudo et al. | |
| 6,481,357 B1 | 11/2002 | Lindner et al. | |
| 6,489,694 B1 | 12/2002 | Chass | |
| 6,527,972 B1 | 3/2003 | Fuchs et al. | |
| 6,530,944 B2 | 3/2003 | West et al. | |
| 6,548,264 B1 * | 4/2003 | Tan et al. | 435/7.21 |
| 6,557,272 B2 | 5/2003 | Pavone | |
| 6,582,429 B2 | 6/2003 | Krishnan et al. | |
| 6,663,673 B2 | 12/2003 | Christensen | |
| 6,666,991 B1 | 12/2003 | Atarashi et al. | |
| 6,683,333 B2 | 1/2004 | Kazlas et al. | |
| 6,734,574 B2 | 5/2004 | Shin | |
| 6,768,230 B2 | 7/2004 | Cheung et al. | |
| 6,789,820 B2 | 9/2004 | Meduvsky et al. | |
| 6,815,063 B1 | 11/2004 | Mayes | |
| 6,871,871 B2 | 3/2005 | Parizat et al. | |
| 6,982,501 B1 | 1/2006 | Kotha et al. | |
| 7,007,972 B1 | 3/2006 | Radhakrishnan et al. | |
| 7,101,862 B2 | 9/2006 | Cochrum et al. | |
| 7,200,956 B1 | 4/2007 | Kotha et al. | |
| 7,249,604 B1 | 7/2007 | Mohanraj | |
| 2001/0011810 A1 | 8/2001 | Saiguchi et al. | |
| 2001/0016210 A1 | 8/2001 | Mathiowitz et al. | |
| 2001/0033384 A1 | 10/2001 | Luo et al. | |
| 2002/0045045 A1 | 4/2002 | Adams et al. | |
| 2002/0164474 A1 | 11/2002 | Buckley | |
| 2003/0009910 A1 | 1/2003 | Pavone | |
| 2003/0216815 A1 | 11/2003 | Christensen | |
| 2004/0002665 A1 | 1/2004 | Parihar et al. | |
| 2004/0022849 A1 | 2/2004 | Castan et al. | |
| 2004/0051283 A1 | 3/2004 | Parizat et al. | |
| 2004/0132562 A1 | 7/2004 | Schwenger et al. | |
| 2004/0154190 A1 | 8/2004 | Munster | |

FOREIGN PATENT DOCUMENTS

| | | |
|---|---|---|
| DE | 37 38 989 A1 | 5/1989 |
| DE | 10240530 | 3/2004 |
| WO | WO 99/53901 | 10/1999 |

OTHER PUBLICATIONS

Azuma, Y. et al. "Coating of ferric oxide particles with silica by hydrolysis of TEOS", Journal of the Ceramic Society of Japan, 100(5), 646-51 (Abstract) (May 1992).

Atarashi, T. et al. "Synthesis of ethylene-glycol-based magnetic fluid using silica-coated iron particle", Journal of Magnetism and Magnetic Materials, 201, 7-10 (1999).

Homola, A. M. et al., "Novel Magnetic Dispersions Using Silica Stabilized Particles", IEEE Transactions on Magnetics, 22 (5), 716-719 (Sep. 1986).

Giri, A. et al. "AC Magnetic Properties of Compacted FeCo Nanocomposites", Mater. Phys. and Mechanics, 1, 1-10 (2000).

U.S. Appl. No. 10/302,962, filed Nov. 25, 2002.

PCT Serial No. PCT/US03/14545—Filed: May 28, 2003.

PCT Serial No. PCT/US03/16230—Filed: Jun. 25, 2003.

Lubbe, AS et al. "Clinical experiences with magnetic drug targeting: a phase I study with 4'- expidoxorubicin in 14 patients with advanced solid tumors", Cancer Research, vol. 56, Issue 20, 4686-4693 (Abstract) (1996).

Sako, M et al., "Embolotherapy of hepatomas using ferromagnetic microspheres, its clinical evaluation and the prospect of its use as a vehicle in chemoembolo-hyperthermic therapy", Gan to kagaku ryoho. Cancer & chemotherapy, vol. 13, No. 4, Pt. 2, 1618-1624 (Abstract) (1986).

Zahn, M. "Magnetic Fluid and Nanoparticle Applications to Nanotechnology", Journal of Nanoparticle Research 3, pp. 73-78, 2001.

Australian Patent Office Examiner's Report dated May 17, 2007 (2 pages).

Derwent Abstract Accession No. 92-223333/27, JP 04149025 A (Toshiba Glass KK) May 22, 1992.

Alam H.B., Chen Z., Jaskille A., Querol R. I. L.C., Koustova E., Incencio R., Conran R., Seufert A., Ariaban N., Toruno K., and Rhee P. Application of a Zeolite Hemostatic Agent Achieves 100% Survival in a Lethal Model of Complex Groin Injury in Swine. J. Trauma. May 2004;56:974-983.

Holcomb J.B., McClain, Pusateri A.E., Beall D., Macaitis J.M., Harris R.A., MacPhee M.J., and Hess J.R. Fibrin Sealant Foam Sprayed Directly on Liver Injuries Decreases Blood Loss in Resuscitated Rats. J. Trauma Aug. 2000;49:246-250.

Ellis-Behnke R.G., Liang, Y.X., Tay D.K.C., Kau P.W.F., Schneider, G.E., Zhang S., Wu W., and So K.F. Nano hemostat solution: immediate hemostasis at the nanoscale. Nanomedicine: Nanotechnology, Biology, and Medicine 2 (2006) 207-215.

Zhou et al., Nanostructures of gold coated iron core-shell nanoparticles and the nanobands assembled under magnetic field. Eur. Phys. J.D. 16, (2001) (Abstract Only).

Office Action dated Oct. 10, 2003, issued in co-pending U.S. Appl. No. 10/681,899, filed Oct. 10, 2003.

Office Action dated Jan. 3, 2008, issued in co-pending U.S. Appl. No. 10/681,899, filed Oct. 10, 2003.

Office Action dated Jan. 20, 2004, issued in co-pending U.S. Appl. No. 10/302,962, filed Nov. 25, 2002.

Office Action dated Oct. 6, 2004, issued in co-pending U.S. Appl. No. 10/302,962, filed Nov. 25, 2002.

Office Action dated Aug. 17, 2005, issued in co-pending U.S. Appl. No. 10/302,962, filed Nov. 25, 2002.

Office Action dated May 30, 2006, issued in co-pending U.S. Appl. No. 10/302,962, filed Nov. 25, 2002.
Office Action dated Aug. 23, 2007, issued in co-pending U.S. Appl. No. 10/302,962, filed Nov. 25, 2002.

Co-pending U.S. Appl. No. 10/681,899, filed Oct. 10, 2003.

* cited by examiner

HEMOSTATIC COMPOSITION

BACKGROUND OF THE INVENTION

The present invention is generally directed to hemostatic compositions, and more particularly to a magnetic hemostatic composition for controlling external or internal bleeding.

Magnetic fluids are magnetic field responsive fluids containing magnetizable particles dispersed in a liquid carrier. These fluids typically have been used in devices, such as dampers, shock absorbers, seals, valves and the like to provide varying stress levels controlled by an external magnetic field. The variable stress is created by magnetic coupling of the particles in the form of chains or bent wall-like structures upon interaction with an external magnetic field. As to the composition, these fluids are typically made of micron-sized particles dispersed in an engineering medium, such as hydraulic oil, mineral oil, or water, or the like.

More recently, the use of magnetic particles has been extended to both in vitro and in vivo applications, including drug targeting, bimolecular separation and detection, and magnetic resonance imaging (MRI). The compositions of such particles are, however, limited only to certain types of iron oxides, for example, magnetite, due to its biodegradibility and biocompatibility. However, many properties of such particles, for example, toxicity and immunological response, are still unknown.

Various prior art methods and compositions disclose the use of hemostatic agents to attenuate bleeding. Examples include U.S. Pat. Nos. 3,047,507; 3,937,839; 4,107,288; 4,268,413; 4,443,430; 4,501,726; 4,554,088; 4,637,394; 4,721,618; 4,992,190; 4,999,188; 5,180,583; 5,202,352; 5,207,675; 5,236,410; 5,354,488; 5,358,659; 5,374,246; 5,427,767; 5,507,744; 5,595,735; 5,624,685; 5,635,162; 5,635,215; 5,645,849; 5,670,078; 5,695,480; 5,702,630; 5,782,954; 5,800,372; 6,036,955; 6,051,607; 6,096,021; 6,189,538; 6,299,619; 6,315,709; 6,335,384 and 6,355,275.

There is a need in the industry, however, for a hemostatic composition or fluid which controls both external and internal hemorrhage.

OBJECTS AND SUMMARY OF THE INVENTION

The principal object of the present invention is to provide a hemostatic composition and/or fluid, which is biologically non-toxic, biocompatible, easily disposable, noninteracting with other biological structures or biomolecules present in the bloodstream, and which can be effectively used to control both internal and external hemorrhage anywhere in the circulatory system of a subject.

An object of the present invention is to provide a hemostatic composition and/or fluid, which is magnetically responsive and exhibits rheological changes upon interaction with an external magnetic field.

Another object of the present invention is to provide a hemostatic composition and/or fluid, which controls or stops bleeding in a very short time, for example, in less than about five minutes.

Yet another object of the present invention is to provide a hemostatic composition and/or fluid, which undergoes a reversible liquid-solid transition under the action of an external magnetic field that causes localized hemostasis at the site of an injury or lesion.

An additional object of the present invention is to provide a hemostatic composition and/or fluid, wherein the particle dispersed therein can be easily produced with tailored dimensions, such as size, shape and distribution, to optimize magnetic response, to make the particles biocompatible and non-toxic, and to easily dispose off the particles after treatment.

An additional object of the present invention is to provide a method of controlling or arresting hemorrhage or bleeding (external or internal) by the use of magnetic particles dispersed in various fluids.

In summary, the main object of the present invention is to provide magnetically responsive and biocompatible particles that, when dispersed in various fluids, exhibit rheological changes upon interaction with an external magnetic field. These fluids, when injected at the site of a lesion or injury, for example, a capillary hemorrhage, form a seal once a magnetic field is positioned adjacent the site of the injury or lesion. The seal formation is due to the formation of particle chains or clusters upon induction of a magnetic moment. The particles range in size from about 5 nm to 10 μm, with shapes, such as spherical, needle-like, oval, etc., and include compositions, such as iron, iron oxides, Ni, Co, etc. To achieve inertness, the particles are preferably coated with gold or silica, and/or polymers, such as poly (ethylene glycol), dextran, sorbitol, and other biocompatible polymers, such as Tween and the like. The use of polymer coating is considered preferable to disperse the particles in carrier liquids, such as saline, ringer's solution, water, blood plasma, and the like. The particle parameters, such as size, shape and magnetism, can be optimized so as to make the particles non-toxic, biocompatible, chemically inert, easily disposable, substantially non-immunogenic, substantially insoluble in blood, and non-interacting with other biological structures or biomolecules present in the blood stream. The application of the present invention include both external and internal hemorrhage as applied to civilian as well as military injuries.

In accordance with the present invention, a hemostatic composition, includes a carrier medium including a predetermined amount of a particulate material. The particulate material is comprised of core particles with a coating. The core particles have an average particle size of about 5 nm to 10 μm, and the coating is one of gold, silica, silver, platinum, steel, cobalt, carbon, a polymer, or a combination thereof.

In accordance with the present invention, a method of controlling bleeding in a subject in need thereof, includes administering to a subject having internal or external bleeding a predetermined amount of a hemostatic fluid including a particulate material in a carrier medium, and applying a magnetic field adjacent the site of a lesion or injury causing the bleeding, so as to form a cluster, coagulation, or agglomeration of the particulate material to thereby prevent the flow of blood through the lesion or injury.

BRIEF DESCRIPTION OF THE DRAWINGS

The above and other objects, novel features and advantages of the present invention will become apparent from the following detailed description of the invention, as illustrated in the drawings, in which.

DETAILED DESCRIPTION OF THE INVENTION

The present invention provides novel approaches to control internal or external hemorrhage using magnetic fluids. The technique can be applied to control bleeding from sites located on the extremities and/or from lacerations involving the femoral or axillary vessels, and also from major vascular or visceral injuries in the body cavities. The novel approach is termed as an Innate Magnetic Tourniquet (IMT). IMT is defined as a tourniquet, which can be applied to all types of hemorrhages (both external and internal), can selectively arrest bleeding only at the site of an injury or lesion without affecting other healthy areas, and is small so that it is portable. An IMT is one of the objectives of the present invention, which serves to magnetically accelerate the coagulation cascade using coated magnetic particles, and preferably paramagnetic or superparamagnetic particles, or a combination thereof (see FIG. 1).

The particles for use in the present invention may be synthesized by various methods, such as chemical synthesis, sol-gel, chemical co-precipitation and microwave plasma technique. The microwave plasma technique, described in pending U.S. application Ser. No. 09/262,848, filed Mar. 5, 1999, now U.S. Pat. No. 6,409,851 (incorporated herein in its entirety by reference) is the preferred technique as it is unique in that it gives better control over particle size, shape and purity, and can be readily extended to produce different compositions of powders. The composition includes a carrier medium and a particulate material of coated core particles, such as iron, iron oxide, cobalt, cobalt oxide, nickel, nickel oxide, or an alloy or a combination thereof. Preferably, the particulate material includes core particle of iron and its oxides.

Figure 2:
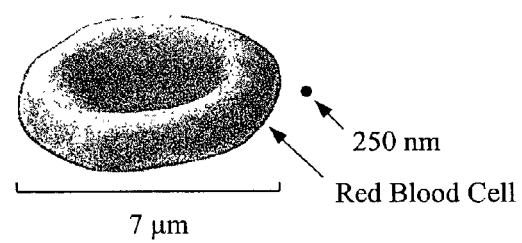
FIG. 2 is an illustration comparing the size of a typical red blood cell to a 250 nm magnetic particle.

The average size of the particles can be from about 5 nm to 10 µm. The preferred size is about 10 nm to 1 µm, while the most preferred size is about 10 nm to 300 nm. The size of the particles is directly related to toxicity, as the particles should be large enough so that they do not get absorbed inside the body, and yet small enough to escape the immunological response of the macrophages. In addition, the particle size also directly translates into the magnetic mass of the mixture, thereby affecting the magnetic properties. FIG. 2 shows a comparison of a 250 nm particle to a typical red blood cell in size. A typical body cell is about twenty-eight times larger than the particle. FIG. 2 also illustrates the importance of proper size selection for the particles.

Figure 3:
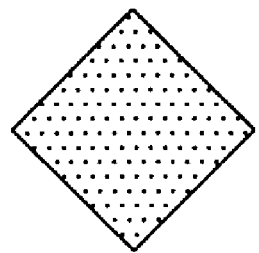
FIG. 3 illustrates various shapes of the particles for use in the present invention.
Figure 3:
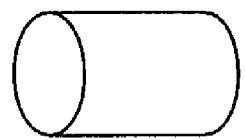
Figure 3:
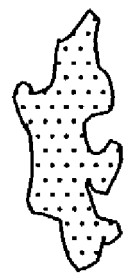
Figure 3:
Figure 3:
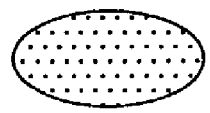
Figure 3:
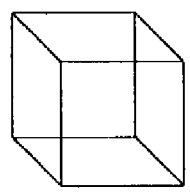
Figure 3:
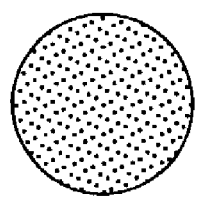

The shape of the particles is important for two reasons. First, the magnetic effect is dependent upon the particle volume fraction, which in turn is a function of the particle shape. For instance, needle-shaped particles exhibit similar magnetic effect at concentrations ten times smaller than spherical particles because of larger surface area per volume. Second, the flow characteristics of the particles in a liquid medium are dependent upon their shape. The shapes utilized in this invention include, but are not limited to, spherical, needle-like, cubic, irregular, cylindrical, diamond, oval, or a combination thereof. FIG. 3 shows preferred particle shapes.

In the present invention, the surface coating on the particles serve several purposes, such as preventing particle agglomeration, rendering the particles biocompatible, preventing dissolution of the magnetic materials, and facilitating either selective interactions with particular biomolecules, such as antibodies and clotting factors, or interactions with specific cell types.

The types of coatings that may be utilized in the present invention, include silica, gold, silver, platinum, steel, cobalt, carbon, a polymer, procoagulant molecules, or a combination thereof. The polymer can be one of polyethylene glycol, dextran, Tween, sorbitol, mannitol, or a combination thereof. The procoagulant molecules can be thrombin or Factor VII a. The most preferred coating is silica or gold. Silica and gold are both effectively inert with respect to dissolution in biological fluids and both are amenable to many types of surface chemical reactions, allowing the surface of the particles to be engineered for various applications.

Many techniques have been developed for depositing controlled silica layers on various substrates, including iron and iron oxide based particles. Some approaches make use of controlled hydrolysis of tetraethylorthosilicate (TEOS) in solutions containing core particles, ethyl alcohol, and ammonium hydroxide. See Azuma, Y. et al. "Coating of ferric oxide particles with silica by hydrolysis of TEOS", Journal of the Ceramic Society of Japan, 100(5), 646-51 (May 1992). The thickness of silica coating can be controlled by varying the reaction conditions.

Other techniques for depositing silica on particles, include acidification of sodium silicate solutions (Atarashi, T. et al. "Synthesis of ethylene-glycol-based magnetic fluid using silica-coated iron particle", Journal of Magnetism and Magnetic Materials, 201, 7-10 (1999)) or controlled heterocoagulation of silica nanoparticles (5-7 nm) with large core particles (Homola, A. M. et al., "Novel Magnetic Dispersions Using Silica Stabilized Particles", IEEE Transactions on Magnetics, 22 (5), 716-719 (September 1986).

In the present invention, a precipitation technique is preferred because of the thin layers that can be achieved. An example of the procedure utilized is provided below in the Example. Sodium silicate is precipitated on the nanoparticle surface to obtain coatings. The amount of sodium silicate can vary from (1 to 80%) depending upon the thickness of the coating desired. The thickness of the coating can be from about 1 nm and 1 µm, but the preferred range is about 5 nm to 50 nm.

In order to obtain gold coatings, an approach developed by Giri et al. "AC Magnetic Properties of Compacted FeCo Nanocomposites", Mater. Phys. and Mechanics, 1, 1-10 (2000) for coating iron particles with other transition metals may be utilized. Magnetic particles are placed in a solution of gold chloride (10-80%), ethylene glycol (5-40%) and water (1585%). The solution is heated, and at high temperatures (between 40° C.-80° C.) ethylene glycol acts as a mild reducing agent, resulting in the formation of a thin coating of metallic gold on the nanoparticles. The thickness of the coating can be from about 1 nm to 1 µm, but the preferred range is about 5 nm to 50 nm.

For in vivo use, magnetic hemostatic (MH) fluids must incorporate water (or a biological medium, such as blood plasma) as the continuous phase. Therefore, there is a need to stabilize the particles (i.e., keep the particles unaggregated and dispersed) in an aqueous carrier fluid, such as water, Ringer's solution, normal saline, sugar solution, blood plasma, or a combination thereof.

Colloidal particles have an inherent tendency to aggregate and form clusters or agglomerate due to attractive van der Waals (vdW) forces. To stabilize the particles against these attractive forces, it is necessary to introduce a repulsive interparticle force, either by an electrostatic or a steric means. Electrostatic stabilization utilizes the surface charge typically present on the particles, which is effective in a medium having a high dielectric constant, such as water, while in steric stabilization, a sufficiently thick layer of a polymeric or surfactant molecules is introduced around the particles. The surface layer functions as a steric barrier to particle aggregation, and thereby ensures the stability of the fluid. This technique is preferred for the present invention. The steric stabilizer for the particles were chosen from, but are not limited to, polyethylene oxide (PEO), dextran, and Pluronic® surfactants (available from BASF).

Magnetic particles are preferably coated with a surfactant by physical or chemical adsorption in a solution phase. Magnetic particles and surfactants in a ratio of 10:1 are mixed under a high-speed shear and ultrasonic irradiation. However, this range can vary from about 1 to 100%, depending upon various material systems. A typical procedure preferred in the present invention for polyethylene glycol coating is described in the Example provided below.

The particle concentration in the final fluid can be about 0.1% to 70% (w/w) depending upon the type of hemorrhage. For example, for an external hemorrhage higher concentrations would be preferable than internal bleeding. Coated particles are dispersed in carrier liquids, and mixing is accomplished under high-speed shear and ultrasonification to form a homogeneous fluid.

EXAMPLE 40 nm spherical iron particles are synthesized by utilizing the microwave plasma technique described in pending U.S. application Ser. No. 09/262,848, filed Mar. 5, 1999, now U.S. Pat. No. 6,409,851 (incorporated herein in its entirety by reference). The particles are mixed with a 10% aqueous sodium silicate solution to obtain a final iron concentration of 20%. The pH of the solution is maintained at about 10 and the suspension is thoroughly mixed. This is followed by slow heating at a temperature of up to 80° C. at which silica precipitates out and forms a coating of approximately 10 nm thickness on the surface of iron nanoparticles. The solution is dried in an oven at a temperature of 110° C. for approximately 12 hours to remove the water. The resulting silica coated iron nanoparticles are dispersed in normal saline at a concentration of 20% using poly(ethylene) glycol (2%) as the surfactant (or dispersing agent). The mixing is accomplished using a high-speed shear mixer for about 3 hours, followed by ultrasonification for about 2 hours. The result is a uniformly dispersed hemostatic fluid which gels upon interaction with an external magnetic field. The magnetic field is generated by using a permanent millimeter sized magnet.

USE AND OPERATION

Figure 1:
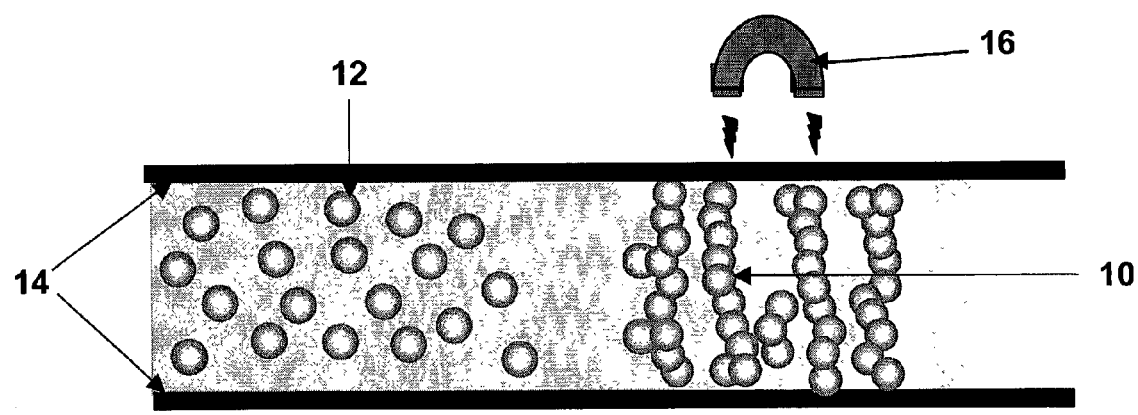
FIG. 1 is a schematic illustration showing the formation of a cluster or agglomeration of the magnetic particles at the site of an injury upon application of a magnetic field.

In order to control internal or external bleeding, an effective amount of the hemostatic composition, preferably in the form of a liquid, is administered to a subject in need thereof. The composition is preferably injected intravenously (or via a catheter) adjacent the site of an injury or lesion 10 so that the particles 12 reach the site of injury 10 in, for example, a blood vessel 14 (FIG. 1). A magnetic field, in the range of about 0.01-3 Tesla, is then applied by using a conventional permanent magnet 16. Due to magnetic induction, the particles 12 would cluster or agglomerate preventing the flow of blood through the lesion 10.

The composition of the invention may also include a conventional marking agent to allow, for example, a surgeon to track the flow of the particles on a scope, etc., in the event a catheter is used to deliver the composition to control internal bleeding.

While this invention has been described as having preferred sequences, ranges, steps, materials, or designs, it is understood that it includes further modifications, variations, uses and/or adaptations thereof following in general the principle of the invention, and including such departures from the present disclosure as those come within the known or customary practice in the art to which the invention pertains, and as may be applied to the central features hereinbeforesetforth, and fall within the scope of the invention and of the limits of the appended claims.

The following references, to the extent that they provide exemplary procedural or other details supplementary to those set forth herein, are specifically incorporated herein by reference.

1. Azuma, Y. et al. "Coating of ferric oxide particles with silica by hydrolysis of TEOS", Journal of the Ceramic Society of Japan, 100(5), 646-51 (May 1992).
2. Atarashi, T. et al. "Synthesis of ethylene-glycol-based magnetic fluid using silica-coated iron particle", Journal of Magnetism and Magnetic Materials, 201, 7-10 (1999).
3. Homola, A. M. et al., "Novel Magnetic Dispersions Using Silica Stabilized Particles", IEEE Transactions on Magnetics, 22 (5), 716-719 (September 1986).
4. Giri, A. et al. "AC Magnetic Properties of Compacted FeCo Nanocomposites", Mater. Phys. and Mechanics, 1, 1-10 (2000).

What is claimed is:

1. A hemostatic composition suitable for controlling external or internal bleeding in a subject, comprising:
    a) a biocompatible and non-toxic carrier medium selected from the group consisting of water, saline solution, sugar solution, Lactose Ringers, blood plasma, and a combination thereof;
    b) a predetermined amount of a particulate material in said medium;
    c) said particulate material comprising core particles with a coating;
    d) said core particles having an average particle size of about 5 nm to 10 μm;
    e) the concentration of said particulate material being about 0.1% to 70% (w/w) of the composition;
    f) said coating comprising procoagulant molecules; and
    g) said core particles comprise a member selected from the group consisting of iron, iron oxide, cobalt, cobalt oxide, nickel, nickel oxide, and an alloy or a combination thereof; and
    h) an optional surfactant or dispersant.
2. The composition of claim 1, wherein:
    a) said core particles have an average particle size of about 10 nm to 1 μm.
3. The composition of claim 1, wherein:
    a) said core particles have an average particle size of about 10 nm to 300 nm.
4. The composition of claim 1, wherein:
    a) said core particles comprise a general shape selected from the group consisting of a sphere, a needle, a cube, an oval, irregular, a cylinder, a diamond, and a combination thereof.
5. The composition of claim 1, wherein:
    a) said core particles comprise clusters.
6. The composition of claim 1, wherein:
    a) said core particles comprise the general shape of blood platelets.
7. The composition of claim 1, wherein:
    a) said coating has a thickness of about 1 nm to 1 μm.
8. The composition of claim 1, wherein:
    a) said coating has a thickness of about 5 nm to 50 nm.
9. The composition of claim 1, wherein:
    a) said procoagulant molecules are selected from the group consisting of thrombin, Factor VII a, and a combination thereof.
10. The composition of claim 1, wherein:
    a) said particulate material is non-toxic to bio-cells or biomolecules.

11. A magnetic hemostatic fluid suitable for controlling external or internal bleeding in a subject, comprising:
a) a biocompatible and non-toxic carrier fluid selected from the group consisting of water, saline solution, sugar solution, Lactose Ringers, blood plasma, and a combination thereof;
b) a predetermined amount of a magnetic particulate material in said carrier fluid;
c) said particulate material comprising core particles with a coating having a thickness of about 1 nm to 10 μm;
d) said core particles having an average particle size of about 5 nm to 10 μm;
e) the concentration of said particulate material being about 0.1% to 70% (w/w) of the hemostatic fluid;
f) said core particles comprising a member selected from the group consisting of iron, iron oxide, cobalt, cobalt oxide, nickel, nickel oxide, and an alloy or a combination thereof;
g) said coating comprising procoagulant molecules; and
h) an optional surfactant or dispersant.

12. The hemostatic fluid of claim 11, wherein:
a) said core particles have an average particle size of about 10 nm to 1 μm.

13. The hemostatic fluid of claim 11, wherein:
a) said core particles have an average particle size of about 10 nm to 300 nm.

14. The hemostatic fluid of claim 11, wherein:
a) said core particles comprise a general shape selected from the group consisting of a sphere, a needle, a cube, an oval, irregular, a cylinder, a diamond, and a combination thereof.

15. The hemostatic fluid of claim 11, wherein:
a) said core particles comprise clusters.

16. The hemostatic fluid of claim 11, wherein:
a) said core particles comprise the general shape of blood platelets.

17. The hemostatic fluid of claim 11, wherein:
a) said coating has a thickness of about 5 nm to 50 nm.

18. The hemostatic fluid of claim 11, wherein:
a) said procoagulant molecules are selected from the group consisting of thrombin, Factor VII a, and a combination thereof.

19. The hemostatic fluid of claim 11, wherein:
a) said particulate material is non-toxic to bio-cells or biomolecules.

20. The hemostatic fluid of claim 11, wherein:
a) the magnetic particles comprise paramagnetic or superparamagnetic particles, or a combination thereof.

21. A method of controlling bleeding in a subject in need thereof, comprising the steps of:
a) administering to a subject having internal or external bleeding a predetermined amount of a hemostatic fluid;
b) the hemostatic fluid, comprising:
  i) a biocompatible and non-toxic carrier fluid selected from the group consisting of water, saline solution, sugar solution, Lactose Ringers, blood plasma, and a combination thereof;
  ii) a predetermined amount of a magnetic particulate material in the fluid;
  iii) the particulate material comprising core particles with a coating having a thickness of about 1 nm to 10 μm;
  iv) the core particles having an average particle size of about 5 nm to 10 μm;
  v) the concentration of the particulate material being about 0.1% to 70% (w/w) of the hemostatic fluid;
  vi) the core particles comprising a member selected from the group consisting of iron, iron oxide, cobalt, cobalt oxide, nickel, nickel oxide, and an alloy or a combination thereof;
  vii) the coating comprising; and
  viii) an optional surfactant or dispersant;
c) applying a magnetic field adjacent the site of a lesion causing the bleeding so as to form a cluster of the particulate material for thereby controlling the flow of blood through the lesion.

22. A hemostatic composition suitable for controlling external or internal bleeding in a subject, comprising:
a) a carrier medium selected from the group consisting of water, saline solution, sugar solution, Lactose Ringers, blood plasma, and a combination thereof;
b) a predetermined amount of a particulate material in said medium;
c) said particulate material comprising core particles with a coating;
d) said core particles having an average particle size of about 5 nm to 10 μm;
e) the concentration of said particulate material being about 0.1% to 70% (w/w) of the composition;
f) said coating comprising procoagulant molecules;
g) said coating further comprising one polymer member selected from the group consisting of polyethylene glycol, dextran, Tween, sorbitol, mannitol, and a combination thereof; and
h) said core particles comprise a member selected from the group consisting of iron, iron oxide, cobalt, cobalt oxide, nickel, nickel oxide, and an alloy or a combination thereof; and
i) an optional surfactant or dispersant.

23. A hemostatic composition suitable for controlling external or internal bleeding in a subject, comprising:
a) a carrier medium selected from the group consisting of water, saline solution, sugar solution, Lactose Ringers, blood plasma, and a combination thereof;
b) a predetermined amount of a particulate material in said medium;
c) said particulate material comprising core particles with a coating;
d) said core particles having an average particle size of about 5 nm to 10 μm;
e) the concentration of said particulate material being about 0.1% to 70% (w/w) of the composition;
f) said coating comprising a member biocompatible and non-toxic to blood cells;
g) said member comprising procoagulant molecules; and
h) said core particles comprise a member selected from the group consisting of iron, iron oxide, cobalt, cobalt oxide, nickel, nickel oxide, and an alloy or a combination thereof; and
i) an optional surfactant or dispersant.

24. A hemostatic composition suitable for controlling external or internal bleeding in a subject, comprising:
a) a biocompatible and non-toxic carrier medium selected from the group consisting of water, saline solution, sugar solution, Lactose Ringers, blood plasma, and a combination thereof;
b) a predetermined amount of a particulate material in said medium;
c) said particulate material comprising core particles with a coating;
d) said core particles having an average particle size of more than 500 nm to about 10 μm;

e) the concentration of said particulate material being about 0.1% to 70% (w/w) of the composition;
f) said coating comprising procoagulant molecules; and
g) said core particles comprise a member selected from the group consisting of iron, iron oxide, cobalt, cobalt oxide, nickel, nickel oxide, and an alloy or a combination thereof; and
h) an optional surfactant or dispersant.

25. The composition of claim 1, wherein:
a) said coating further comprises a biocompatible and non-toxic member selected from the group consisting of gold, silica, silver, platinum, steel, cobalt, carbon, a polymer, and a combination thereof.

26. The hemostatic fluid of claim 11, wherein:
a) said coating further comprises a biocompatible and non-toxic member selected from the group consisting of gold, silica, silver, platinum, steel, cobalt, carbon, a polymer, and a combination thereof.

27. The method of claim 21, wherein:
a) the coating further comprises a biocompatible and non-toxic member selected from the group consisting of gold, silica, silver, platinum, steel, cobalt, carbon, a polymer, and a combination thereof.

28. The composition of claim 23, wherein:
a) said coating further comprises a member selected from the group consisting of gold, silica, silver, platinum, steel, cobalt, carbon, a polymer, and a combination thereof.

29. The composition of claim 24 wherein:
a) said coating further comprises a biocompatible and non-toxic member selected from the group consisting of gold, silica, silver, platinum, steel, cobalt, carbon, a polymer, and a combination thereof.

30. The composition of claim 25, wherein: a) said polymer is selected from the group consisting of polyethylene glycol, dextran, Tween, sorbitol, mannitol, and a combination thereof.

31. The hemostatic fluid of claim 26, wherein: a) said polymer is selected from the group consisting of polyethylene glycol, dextran, Tween, sorbitol, mannitol, and a combination thereof.

* * * * *